United States Patent
Tzipori et al.

(10) Patent No.: US 9,522,350 B2
(45) Date of Patent: Dec. 20, 2016

(54) METHOD AND DEVICE FOR THE CONCENTRATION OF MULTIPLE MICROORGANISMS AND TOXINS FROM LARGE LIQUID TOXINS

(71) Applicants: TRUSTEES OF TUFTS COLLEGE, Medford, MA (US); HAEMONETICS CORPORATION, Braintree, MA (US)

(72) Inventors: Saul Tzipori, Shrewsbury, MA (US); Udi Zukerman, Brookline, MA (US); Gary Stacey, Marshfield, MA (US)

(73) Assignees: Trustees of Tufts College, Medford, MA (US); Haemonetics Corporation, Braintree, MA (US)

( * ) Notice: Subject to any disclaimer, the term of this patent is extended or adjusted under 35 U.S.C. 154(b) by 0 days.

(21) Appl. No.: 14/079,325

(22) Filed: Nov. 13, 2013

(65) Prior Publication Data
US 2015/0151221 A1    Jun. 4, 2015

Related U.S. Application Data

(63) Continuation of application No. 12/602,819, filed as application No. PCT/US2008/066894 on Jun. 13, 2008, now Pat. No. 8,614,083.

(60) Provisional application No. 60/934,417, filed on Jun. 13, 2007.

(51) Int. Cl.
| | |
|---|---|
| *B04B 5/10* | (2006.01) |
| *B01D 21/26* | (2006.01) |
| *B03C 3/15* | (2006.01) |
| *B03C 5/02* | (2006.01) |
| *B01D 21/30* | (2006.01) |
| *G01N 1/40* | (2006.01) |

(52) U.S. Cl.
CPC .......... *B01D 21/262* (2013.01); *B01D 21/302* (2013.01); *B03C 3/15* (2013.01); *B03C 5/02* (2013.01); *B04B 5/10* (2013.01); *G01N 1/4077* (2013.01); *B01D 2221/10* (2013.01); *B03C 2201/26* (2013.01)

(58) Field of Classification Search
None
See application file for complete search history.

(56) References Cited

U.S. PATENT DOCUMENTS

| | | | |
|---|---|---|---|
| 2,594,445 A | | 4/1952 | Keith, Jr. |
| 5,543,056 A | * | 8/1996 | Murcott et al. ............... 210/705 |
| 5,688,588 A | | 11/1997 | Cotton et al. |
| 6,193,896 B1 | * | 2/2001 | Kim et al. ..................... 210/767 |
| 6,464,624 B2 | | 10/2002 | Pages |
| 6,645,388 B2 | * | 11/2003 | Sheikh-Ali ................... 210/767 |
| 2001/0040136 A1 | * | 11/2001 | Wei et al. ..................... 210/767 |
| 2003/0054934 A1 | | 3/2003 | Brown et al. |
| 2005/0098507 A1 | | 5/2005 | Dolecek |
| 2005/0118570 A1 | | 6/2005 | Hollis et al. |
| 2006/0070952 A1 | | 4/2006 | Jin et al. |

OTHER PUBLICATIONS

Zuckerman et al., Journal of Applied Microbiology 86(6): 955-961 (1999). "Evaluation of a portable differential continuous flow centrifuge for concentration of Cryptosporidium oocysts and Giardia cysts from water."

Payment et al., Appl. Environ. Microbiol. 59(8): 2418-2424 (1993). "Clostridium perfringens and somatic coliphages as indicators of the efficiency of drinking water treatment for viruses and protozoan cysts."

* cited by examiner

*Primary Examiner* — Robert Yamasaki
(74) *Attorney, Agent, or Firm* — Nixon Peabody LLP (57) ABSTRACT

A method for the simultaneous concentration of multiple toxins from large volumes of water. The method includes the steps of providing a disposable separation centrifuge bowl, the centrifuge bowl including a positively charged material at it's inner core. A large water sample contaminated with toxins from a group consisting of protozoa, bacteria, bacterial spores, and toxins is delivered to the centrifuge bowl. A centrifugal force is applied to the separation bowl. The water sample is concentrated to remove large particles of the toxins in the bowl due to the centrifugal forces. The concentrated water sample is passes through the positively charged inner core to capture any remaining concentrated targets by electrostatic forces and the concentrated targets are eluted.

8 Claims, 11 Drawing Sheets

METHOD AND DEVICE FOR THE CONCENTRATION OF MULTIPLE MICROORGANISMS AND TOXINS FROM LARGE LIQUID TOXINS

CROSS REFERENCE TO RELATED APPLICATIONS

This application is a divisional application of U.S. patent application Ser. No. 12/602,819, now issued as U.S. Pat. No. 8,614,083 on Dec. 24, 2013, which is a 35 U.S.C. §371 National Stage of International Application No. PCT/US2008/066894 filed on Jun. 13, 2008, which designates the United States, and which claims the benefit of priority under 35 U.S.C. §119(e) of U.S. provisional application No. 60/934,417, filed Jun. 13, 2007, the contents of each of which are hereby incorporated herein by reference in their entireties.

GOVERNMENT SUPPORT

This invention was made with United States Government support under Grant No. RD83300301 awarded by the Environmental Protection Agency, and Grant No. W911NF-07-C-0030 awarded by the Army Research Office. The United States Government has certain rights in the invention.

BACKGROUND OF THE INVENTION

1. Field of the Invention

The present invention relates to a method and device for the simultaneous concentration of multiple waterborne pathogens from large volumes of liquid toxins, and more particularly to the effective concentration of small numbers of multiple waterborne pathogens from large volumes of various water matrices.

2. Description of the Related Art

Effective concentration of small numbers of multiple waterborn pathogens from large volumes of various water matrices is a serious challenge. Current commercially available technologies are not able to automatically concentrate and elute simultaneously multiple pathogens from large liquid volumes using portable equipment. Pathogens size, variability and biological differences requires the use of specific, expensive, and labor intensive concentration techniques, especially for viruses and protozoa.

Currently, the two major approaches for concentrating multiple microorganisms from large water volumes include filtration and continuous flow centrifugation. Ultrafilters, which organisms are retained by size exclusion have much smaller pore size than viruses, which allow for the simultaneous concentration of viruses, bacteria, and protozoa. The particles are kept in the retentate and thus prevent clogging of the filter surface. Several publications have described the application of hollow fiber ultrafilters for concentrating human viruses, see Bicknell, 1985, *Cryptosporidium* oocysts (Simmons, 2001; Kuhn and Oshima, 2002, Ferguson, 2004), and the simultaneous concentration of viruses, bacteria and protozoa (Juliano and Sobsey, 1997/1998; Morales-Morales, 2003; Hill 2005).

However, ultrafiltration methodology is cumbersome and requires further systematic evaluation for much larger volumes of water than the 100 L volumes that are currently available. Electropositive filters are not rated by pore size and were initially designed to capture viruses from large water volumes by electrostatic attraction. There have been a few publications that evaluated their efficacy to concentrate bacteria and protozoa. See Hou et al, (1980) which reported substantially high retention of *E. coli*, Viruses (Polio, and MS2 bactenophages, and endotoxin) by using charged modified filters. Watt et al. (2002) reported low recoveries for *Cryptosporidium* oocysts, *Giardia* cysts and Polio virus from large water volumes, 14% and 17%, respectively.

Recently, two configurations of the ZetaPlus® Virosorb® 1 MDS filter were evaluated for simultaneous recovery of multiple microorganism types from tap water (Polaczky et al., 2007). High numbers of *C. parvum, S. enterica* and *B. globigii*, and bacteriophages, were spiked into 25 L of tap water samples. Low recoveries were achieved using the cartridge filter, 21%, 37%and 87%, respectively and much higher recoveries, 28%, 50%, 65%, respectively, were reported for the flat filter.

Continuous flow centrifugation (CFC) enables large scale collection of particles, such as protozoa and bacteria, through their sedimentation due to high centrifugal forces. Whitmore and Carrington, (1993) employed a bench-top centrifuge for the recovery of *C. parvum* oocysts from water samples.

Utilization of stationary bench-top blood cell separators with recoveries of several folds higher than the cartridge filtration was also reported (Goatcher, 1996). Substantially high recoveries (>90%) were reported for simultaneous concentration of *Cryptosporidium, Giardia, Microsporidium*, and bacteria from small volumes of source and potable water using a stationary centrifuge and a costly labor-intensive protocol (Borchardt and Spencer 1996; Borchardt and Spencer, 1998; Borchardt and Spence 2002).

However, less efficient recoveries of *C. parvum* oocysts from 100 L were also reported by this method (Swales and Wright, 2000). In addition, very low recoveries, less than 5%) of *C. parvum* from 10 L of water spiked source water, using a compact continuous flow centrifuge were reported (Higgins, 2003).

The above reports demonstrate that currently suggested approaches for concentrating multiple microbe types from large water samples are limited by manually operated systems, using expensive disposables and employing tedious protocols that are not suitable for rapid response to accidental or deliberate water contamination and may complicate routine monitoring.

An earlier prototype of a modified blood separation apparatus, such as the 625B standard disposable bowl manufactured by Haemonetics, of Braintree, Mass.) efficiently concentrated *Cryptosporidium* oocysts, *Giardia* cysts, and *Microsporidian* spores from tap and source water samples. The basic principle underlying the Continuous Flow Centrifugation (CFC) technique has also been described (Zuckerman et al, 1999; Zuckerman and Tzipori, 2004; 2006).

However, there still exists the need for a continuous flow centrifuge that enables concentration and elution of targets from large volumes of liquids.

SUMMARY OF THE INVENTION

One aspect of the present invention is to provide an automated portable continuous flow centrifuge that enables complete automation of the concentration and elution of the targets from large volumes of liquids.

Immediate and anticipated uses and/or commercial applicability of the continuous flow centrifuge of the present invention include: the simultaneous concentration of viruses, protozoa, bacteria, bacterial spores, algae, and toxins from large volumes of liquids such as water, wastewater, milk, wine, beverages and other liquids; on line monitoring of microbial quality of liquids; and on line monitoring of biothreat agents in liquids The device is simple to operate, rapid, robust and portable. The device can also be easily upscaled to concentrate larger volumes. The process of sample concentration and elution is completely automated and the resulting concentrate is small in volume and presentable to a variety of detection methods.

In accomplishing these and other aspects of the present invention, there is provided a method for the simultaneous concentration of multiple toxins from large volumes of water. The method includes the steps of providing a disposable separation centrifuge bowl, the centrifuge bowl including a positively charged material at it's inner core. A large water sample contaminated with toxins from a group consisting of protozoa, bacteria, bacterial spores, and toxins is delivered to the centrifuge bowl. A centrifugal force is applied to the separation bowl. The water sample is concentrated to remove large particles of the toxins in the bowl due to the centrifugal forces. The concentrated water sample is passes through the positively charged inner core to capture any remaining concentrated targets by electrostatic forces and the concentrated targets are eluted.

There is further provided a device for concentrating multiple pathogens from large liquid samples. The device includes a centrifuge bowl and a core including a positively charged material located within the centrifuge bowl. An inlet located at one end of the bowl receives the liquid sample containing the pathogens. The core has a passageway and the liquid sample flows through the core and the concentrated pathogens are attracted and adhere to the positively charge material.

These and other objects, features, aspects, and advantages of the present invention will become more apparent from the following detailed description of the preferred embodiment relative to the accompanied drawings, in which:

BRIEF DESCRIPTION OF THE DRAWINGS

FIG. 1 is a perspective view of the portable concentrator of the present invention.

FIG. 2 is a perspective view of the top deck of the concentrator housing.

FIG. 3 is a perspective view of the rear panel of the concentrator housing.

FIG. 4 is a perspective view of the pump of the concentrator.

FIG. 5 is a perspective view of the large pneumatic valve of the concentrator.

FIG. 6 is a perspective interior view of the concentrator of the present invention.

FIG. 7 is a perspective view of a partially cut away high separation bowl of the present invention.

FIG. 8 is an outer view of the core of the HS separation bowl of the present invention.

FIGS. 9A and 9B are cross-sectional views of the inner and outer cores of the HS separation bowl of the present invention.

FIG. 10 is a top view of the loading diagram of the disposable set.

FIG. 11 is a flow diagram of the operation of the concentrator of the present invention.

DETAILED DESCRIPTION OF THE PREFERRED EMBODIMENTS

The automated portable concentrator of the present invention simultaneously concentrates protozoa, bacteria, bacterial spores, and toxins from large volumes of liquids. After completion of the concentration cycle it elutes the concentrated targets and delivers the concentrate to disposable sterile bags that can be presented in the field to various detection kits or can be sent to a lab for analysis. The concentrate could also be presented to a variety of detection methods.

As will be described in further detail herein, the portable continuous flow device includes a disposable bowl that simultaneously concentrates multiple pathogens from the same sample, and an automated portable continuous flow centrifuge that accommodates the modified bowl and a disposable tubing harness and allows for sample concentration and elution from large water volumes.

Referring to FIG. 1, the CFC100A™ concentrator 10 houses a centrifuge 12, such as that made by Magstar Technologies of (Minneapolis, Minn.) and which is capable of running from 0 to 12,000 rpm (max 400 RCF), a peristaltic pump 14 (0-1000 ml/min), various high pressure pneumatic valves 16, 18 and electronics that are all controlled by a PLC computer system (FIG. 6) enclosed in a housing 20. Display housing 20 is compact and light, measuring, for example, 12×13×16 inches tall and weighing 30 pounds. The PLC system has a preset protocol for 10 L sample volumes, but can be programmed for larger volumes. It is also capable of storing numerous different protocols giving the machine a great deal of versatility and flexibility. The power source can be a versatile 240/110 VAC and there is an optional transport and storage cart which houses a rechargeable battery pack to run the machine with DC power. A cover 22 is hinged to top deck 24. The housing 20 and cover 22 and can be made from a 5051 aluminum or other suitable material. It should be appreciated that the described dimensions of the housing and the operating parameters of the components are examples only and each can be adjusted depending upon the applications of the present invention.

Housing 20 includes a base 21 and a top deck 24 to which centrifuge 12 and pump 14 are mounted. Motor control units (not shown) to control the centrifuge and pump speeds are also mounted within the base. Pluralities of pinch valves 16, 18 are also mounted on the top deck. For example, two large valves 18 and three small valves 16 are provided to control the tubing flow. The PLC control and pneumatic module for the pinch valves can also be mounted to the inside of the top deck.

As shown in FIG. 2, top deck 24 includes a plurality of apertures 25-27 for the centrifuge, valves, and pump. A seal (not shown) can be placed around the hole 25 in the top deck for the centrifuge and at the back between top deck 24 and cover 22 to prevent against water leakage into the concentrator. Base 21 also includes a rear panel 28 as shown in FIG. 3. Rear panel 28 has three sides that complete the base of the housing. A cooling fan 30 is mounted to the rear panels. A power entry module can also be mounted at 32 and recessed handles 34 are also located on the panel sides.

Referring to FIG. 4, pump 14 is used to control the direction and flow rates of fluids during the concentration and elution procedures. Pump 14 can include for example, three pump rollers that are spring loaded with three springs per roller and slide in a miter groove. Such a configuration is sufficient for a ⅜" tubing. Pump 14 includes a rotor 36 that is driven by a pump motor 36 using a mating square configuration between the motor shaft and the rotor. A shaft of the motor is attached to the rotor by a threaded cap. Pump 14 includes a pump platen 40 that pivots at one end in nylon bushings to allow tubing to be threaded through the pump.

Rotor 36 and platen 38 are designed for high volume blood processing. The pump motor can be a brushless stepper that allows flow rates, for example, between 1 LPM to 0. A rotor guard 42 is fixed to the base 21 and encloses the rotor to protect the operator from rotating parts. A platen sensor arm 44 is located on the platen shaft. If the platen is opened during pump operation the pump will come to a stop.

Figure 5:
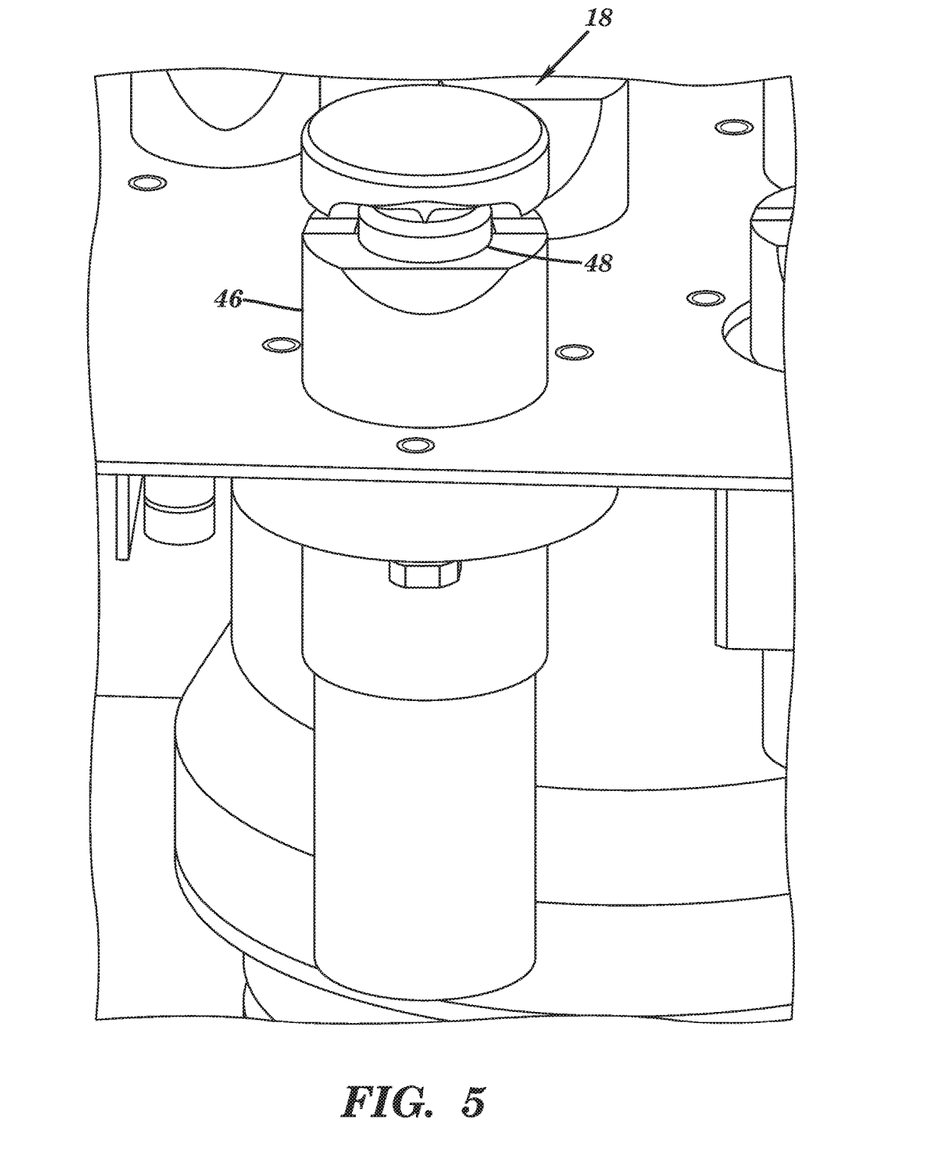

As described above, a plurality of pneumatic valves 16, 18 are provided. Referring to FIG. 5, large pneumatic valve 18 includes a valve housing 46 and a valve assembly 48. Both are attached to the underside of top deck 24. Valve assembly 48 is located within valve housing 46. O-rings can be provided to prevent leakage. Air pressure keeps the valve open while spring pressure keeps it close. Valve housing 46 can be made of hard coated 6061 aluminum or another appropriate material. Small pneumatic valves 16 can be a one-piece assembly, for example, those made by Aerodyne Controls of Ronkonkoma, N.Y.

Figure 6:
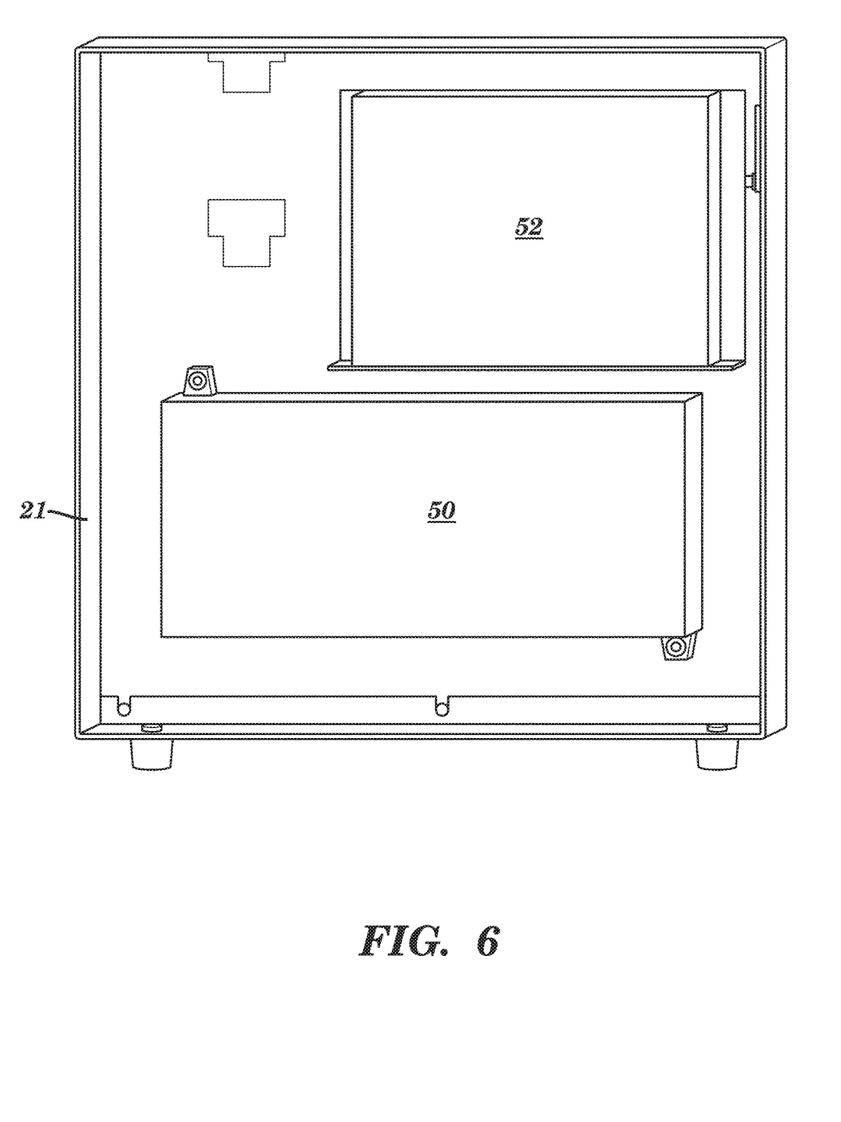

Referring to FIG. 6, the concentrator 10 includes a PLC 50 located within base 21. PLC can have numerous inputs, outputs and communication ports used for programming, operation interfaces or networking, as is known in the art and can be similar to the PLC manufactured by Automation Direct of Atlanta, Ga. One communication port should be multi-functional and capable of handling RS485, RS232C, and RS422 communication links. Over 220 different instructions are available for program development, as well as, extensive internal diagnostics that can be monitored from the application program or from an operator interface. Handheld programmers, operator interfaces or a personal computer can be easily connected without the need for any additional hardware. The PLC can be operated on 24 volt DC power. Also, PLC 50 can operate with Boolean ladder instruction programming that uses 16-bit register virtual memory for data storage. Software, such as DL06PLC or DirectSOFT5 for Windows® installed on a personal computer cabled to the PLC. Program storage can be via FLASH memory that is part of the CPU board in the PLC. In addition, RAM within the CPU can store system parameters, Virtual Memory and other data that is not in the application program. The RAM can be backed up by a super-capacitor, storing the data for several hours in the event of a power outage. The capacitor can automatically recharge during powered operation of the PLC. A pneumatics module 52 is also located within base 21. Pneumatics module 52 is designed to supply air pressure to pneumatic valves 16 and 18. The CFC contains two motor controllers, one for the centrifuge and one for the pump.

The CFC is powered by and an Astrodyne MK75s-24, which has and input voltage range of 90-264 VAC and an output voltage of 25 VDC. A relay is used for communication between the PLC and the motor controllers and can be a 70-782EL8-1 socket relay, manufactured by Magnacraft of Milwaukee, Wis., and is an eight pin logic style DIN panel with an elevator terminal or module compatible relay. It has a normal voltage rating of 300 volts and a normal current rating of 12 amps.

An EMI filter, such as that manufactured by Filter Concepts of Santa Ana, Calif., is designed to effectively attenuate differential and common mode noise from switch mode power conversion and regulation circuits subject to FCC Class B or CISPRJEN Class A conducted EMI limits. Maximum attenuation is achieved at 150 kHz and above. The filter is also available with an A-circuit option to enhance its performance in applications with high source impedance.

Figure 7:
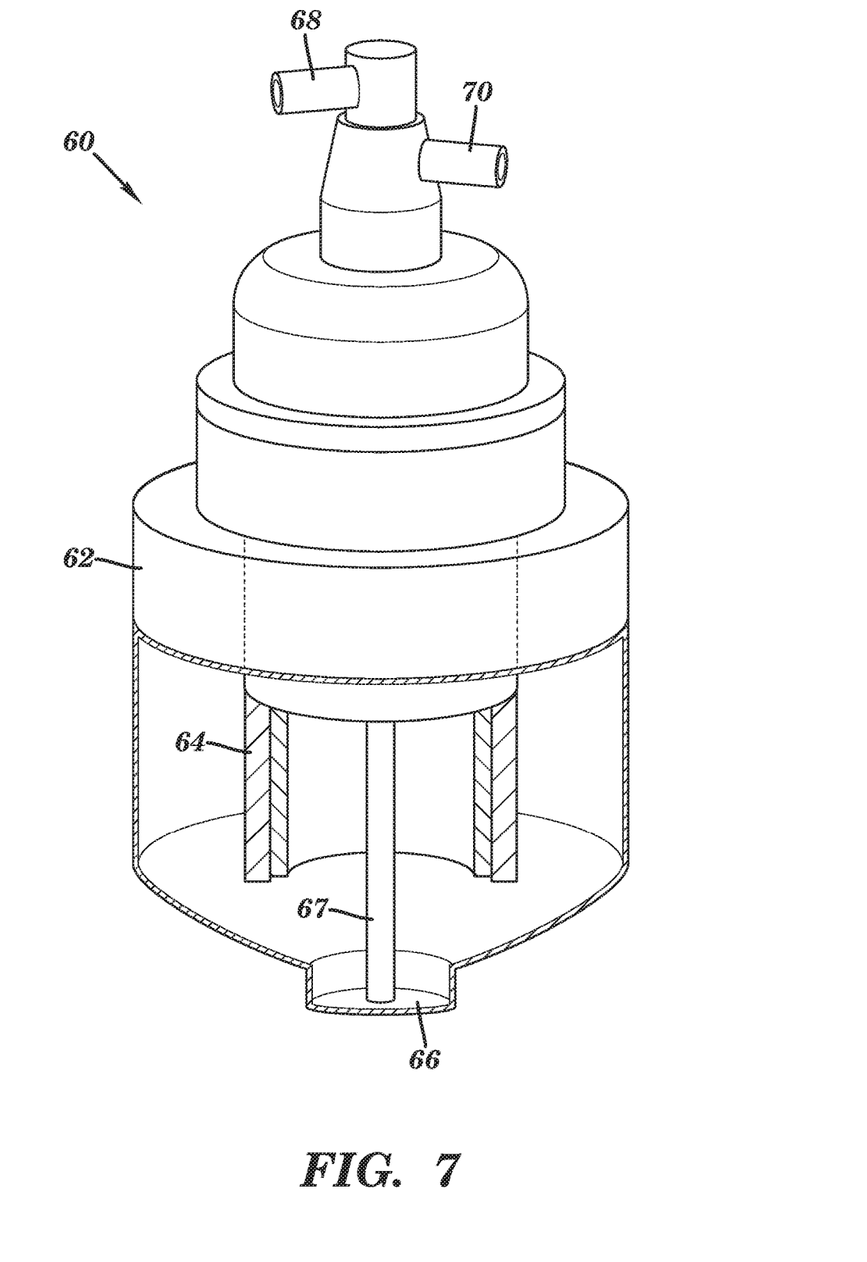

The present invention also provides for a sterile, disposable set 58 (FIG. 10) that includes a high separation core bowl, PVC tubing and at least two collection bags required for the concentrated sample's elute. The disposable set is packaged separately in a sealed bag and ETO sterilized. Referring to FIG. 7, a high separation disposable bowl 60 includes a bowl 62 and a two-piece core 64, which will be described further herein, located within bowl 62. HS bowl 60 is designed to be placed within centrifuge 12. At one end bowl 62 is a basin 66 in which, protozoa, bacteria, and other large particles are compacted and from which virus buffer is collected depending upon the stage of operation of the concentrator. Located at the other end of bowl 62 is an inlet port 68 through which a water sample is delivered to the HS bowl. An outlet port 70 is also located at the end of the bowl through which virus buffer is injected during a certain stage of operation. An inner fluid passageway 67 travels through the core.

Figure 8:
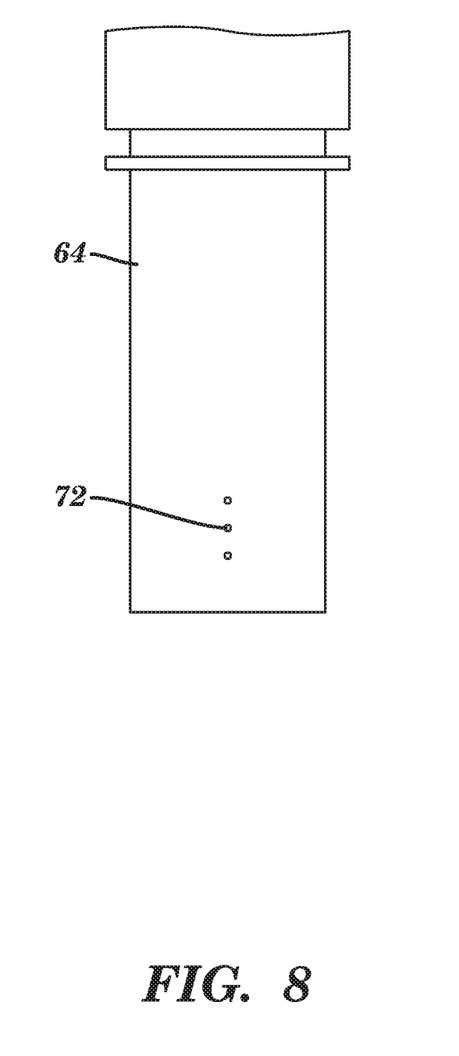
Figure 9A:
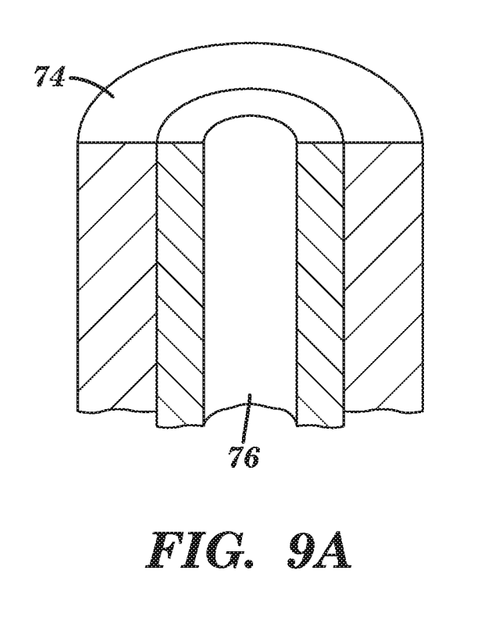
Figure 9B:
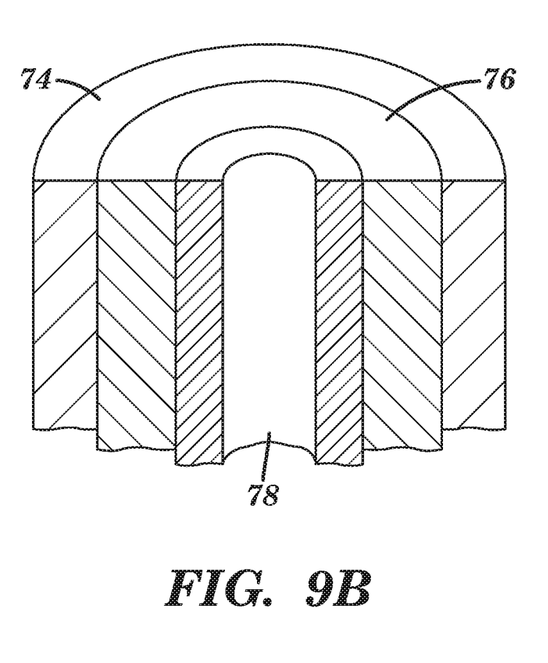

Referring to FIGS. 7 and 8, the two-piece core 64 is a modification of a core manufactured by Heaomonetics. The core includes a plurality of holes 72 drilled around the lower perimeter of the core to allow for a homogeneous flow of water through charged material of the core, which will be described herein. For example, six sets of three holes at 45 degree increments can be drilled around the lower perimeter, for a total of 24 holes. As shown in FIGS. 9A and 9B, core 64 includes an outer core 74 and an inner core 78. Located between cores 74 and 78 is a layer of positively charged filter material 76. Charged filter material 76 will be further described herein.

As mentioned above, the portable equipment uses disposable set 58 that uses ⅜" outside diameter by ¼" inside diameter large tubing, 3/16" outside diameter by ⅛ inside diameter small tubing, bowl 60 and two plastic bags (100 ml for the viruses and 400 ml for the protozoa/bacteria). During the concentration process, the large diameter tubing delivers the liquid samples to the pump and into the disposable bowl. The large particles (protozoa, bacteria, spores, suspended material and debris) are sedimented, the "cleaner" liquid which contains negatively charged viruses/toxins is forced through the core and viruses and toxins are captured by strong electrical force. Then, the large tubing directs the waste water from the machine. During the automated elution process, the small tubing directs the protozoa/bacteria buffer into the bowls residual and also delivers the virus buffer into the core. The large bag initially accommodates the protozoa/bacteria buffer and after the elution it contains the protozoa/bacteria concentrate. The small bag contains the virus buffer and retains the virus concentrate.

Figure 10:
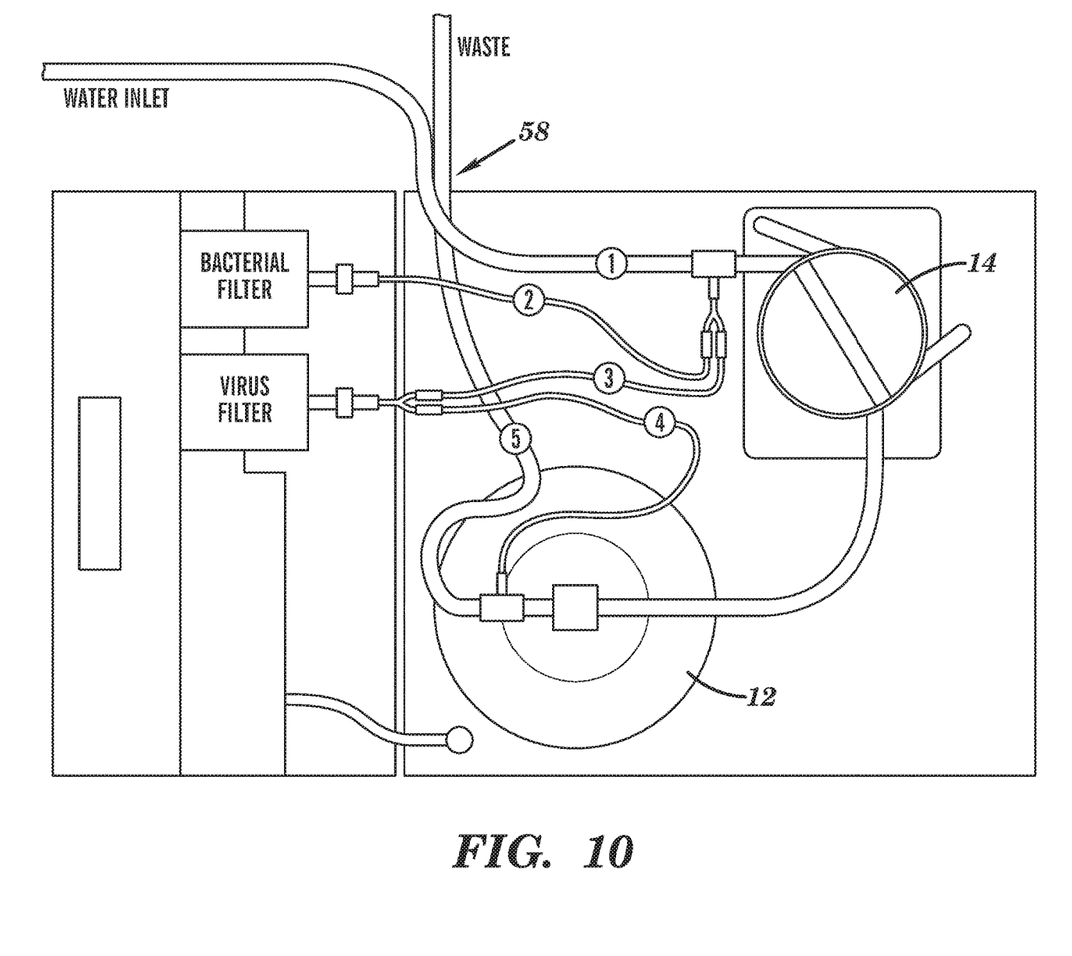

Referring to FIG. 10, the large diameter tubing is attached to the inlet and outlet ports of the HS core bowl, which is held in the centrifuge chuck. As shown, the pump drives the water sample through the large diameter tubing to the inlet port of the bowl. Waste water is carried through large diameter tubing from the outlet port of the bowl. During the elution process the small tubing carries the elution buffers from the bags to the centrifuge bowl and carries the concentrate eluate back to the bags when the elution cycle concludes. The set is coupled by a variety of PVC connectors. The high separation core bowl 60 includes positively charged material and a membrane welded to the top to retain the material.

As described above, disposable continuous flow centrifuge bowl 60 has a positive charged matrix for virus capturing, simultaneously with bacteria, protozoa and toxins. The positive charged core allows for simultaneous concentration of protozoa, bacteria, spores, toxins and viruses, from large water volumes.

Two different techniques were used to prepare the charged component. The first configuration was prepared as follows: the outer glass fiber covers of a 12"×9.5" sheet of ViroCap viral filter manufactured by Argonide Co. of Sanford, Fla., were gently peeled away, removing them from the inner membrane filter. This inner membrane filter was then cut into strips, placed into a blender, and shred to a consistency of "cotton". The same was repeated with an equal volume of tissue paper. An equal weight of 15 grams each of ViroCap viral filter "cotton", and tissue "cotton" were then added to one bag containing 10 grams of aluminum hydroxide Al(OH)$_3$ nano-ceramic fibers Boehmite R0608 by Argonide Co. The bag was then sealed and mixed thoroughly, so as to evenly distribute all materials.

The out flow chamber of the core was then packed with the final product of the filter material prep. To further ensure a homogenous mix, the volume of filter material prep for each core, approximately 4 grams, were teased apart and mixed manually before being inserted into the core. A 6" thin plastic ruler was used to pack the prepped material into the core out flow chamber, a consistent and form an optimal homogenous, dense but fluffy filter matrix. A fiber cover support, for example, Hollytex 3267 spunbond polyester, Haemonetics part #50996-00, made by Ahlstrom Technical Specialties of Mt. Holly Springs, Pa., was cut to fit to seal the top of the out flow chamber, securing the filter material prep within the out flow chamber.

A second configuration involved the preparation of a slurry composed of 1 g Pyrex fiber glass wool, 8 micron pore size, borosilicate such as Aldrich CLS3950 manufactured by Sigma of St. Louis, Mo., 1 g of nano-ceramic Boehmite fibers powder, for example, R0608 of Argonide Corp., of Sanford, Fla.) and 1 g of cellulose microcrystalline powder (Aldrich 435236 by Sigma), 1 g of paper pulp, and 5 ml of DI water which was mixed thoroughly, and was poured into the inner space of the bowl's insert. The insert was then placed in a dry oven overnight at 70° C. Both types of modified cores were then sent to Haemonetics and used in the final assembly of the HS plasma aphaeresis bowls.

The present invention also encompasses a continuous flow centrifugation methodology which allows for the simultaneous concentration and processing of protozoa, bacteria, viruses, and toxins presented in large water volumes. The overall process involves the following steps: a) concentration; and b) elution. In the concentration step, the peristaltic pump delivers a water sample through the bowl's inlet port 68, the large particles such as protozoa, bacterial spores/cells and other suspended material is sedimented due to the strong centrifugal forces and the much cleaner water sample is forced to flow through the designated passages in the bottom of the inner core, where as the negatively charged viruses are captured by the strong electrostatic attraction, eliminates clogging issues that are common in standard filtration components.

During elution protozoa/bacteria are dislodged by the addition of detergent and agitation, and the viruses which are trapped in the virus matrix are released using a protein buffer which inverts the negative charge. Both the virus and protozoa/bacteria concentrates are delivered to a sterile bag. The bags could be processed in the field by using portable detection kits or delivered to the laboratory.

Figure 1:
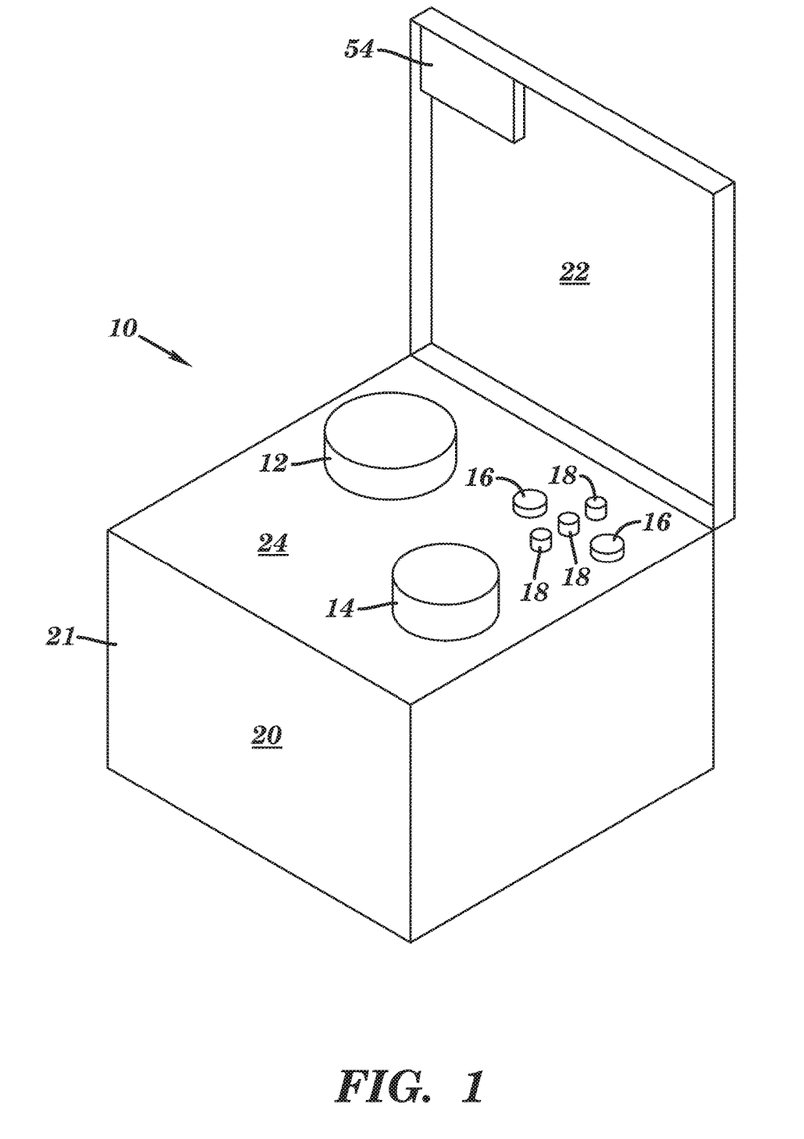
Figure 2:
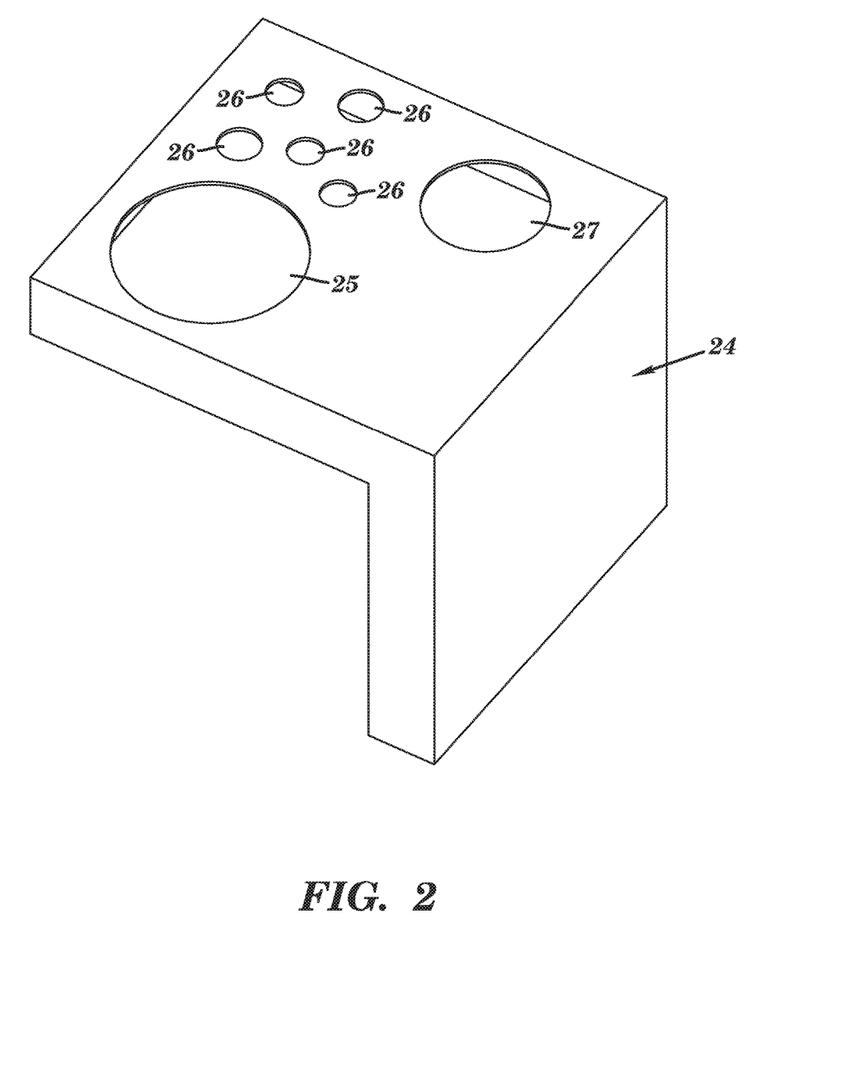
Figure 3:
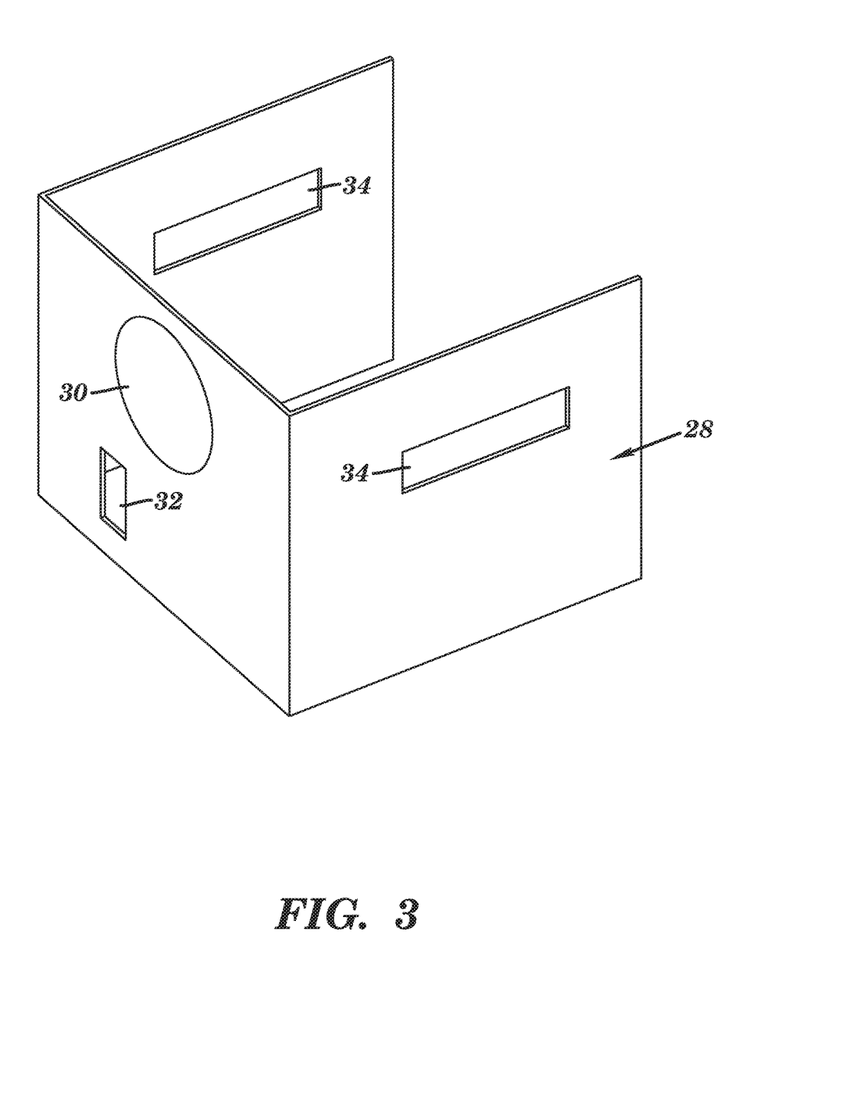
Figure 4:
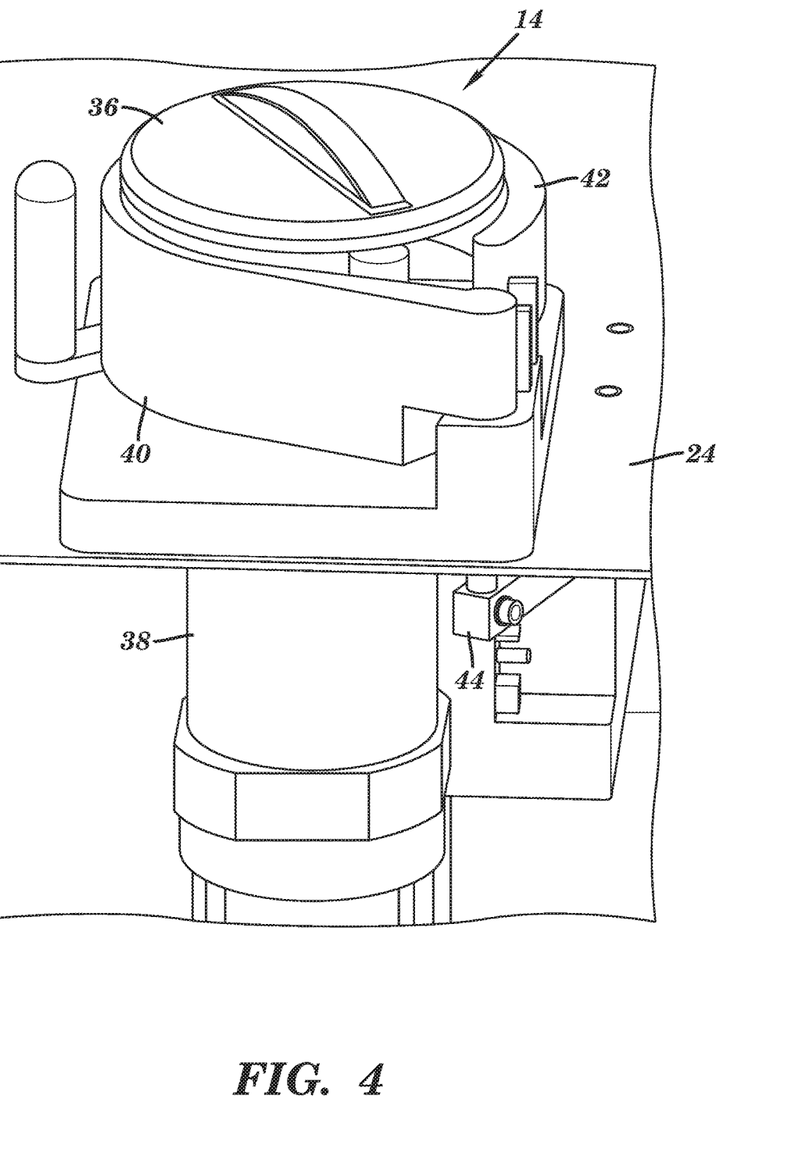
Figure 11:
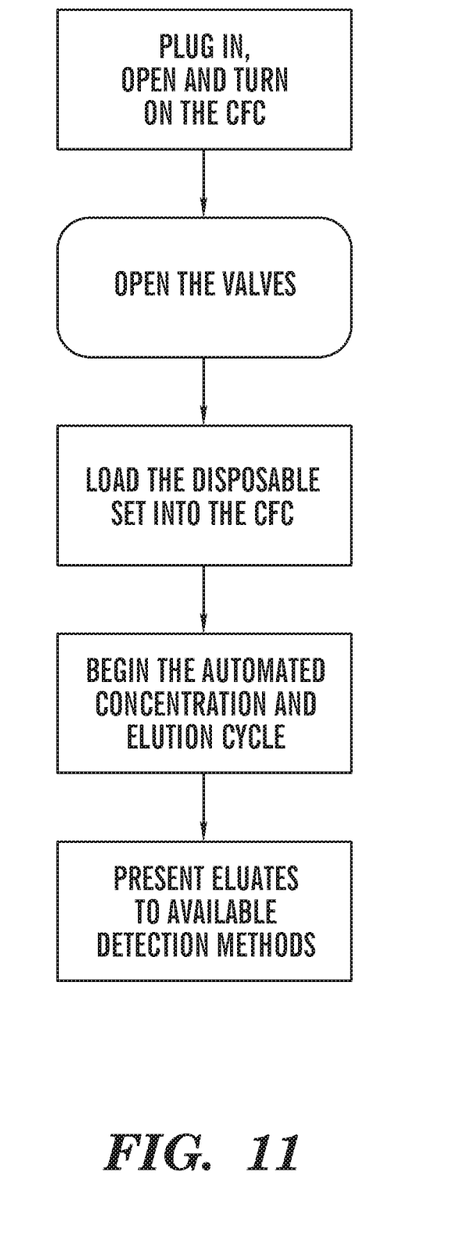

Referring to FIGS. 10 and 11, the operation of the concentrator of the present invention will be described. The concentrator is started and the display panel 54 (FIG. 1) will read "Press Select." When the select button is pressed all of the valves 16, 18 are opened. The centrifuge door is opened. A new, sterile disposable set 58 is opened and removed from its packaging. The HS disposable bowl 60 is inserted into centrifuge 12 and the centrifuge door is closed and locked. Next, the large diameter inlet tube is connected to the inlet port of the bowl and thread through the pump leaving the pump stop on the outside of the guard. The pump platen is closed and the inlet tube is pressed into valve 1. The large diameter outlet tube is then connected to the outlet port of the bowl and press fitted into valve 5. The bags containing the elution buffers on hooks on the cover. The tubing connected to the bacteria elution bag is pressed into pinch valve 2. The remaining tubing is press-fitted into valves 3 and 4. The select button on the display is pressed to close all the valves. The slide clamps on the tube of each bag containing the elution buffers are then opened. To begin concentration, the inlet tube is placed into the water sample and the outlet tube is positioned within the waste container. The start button on the display panel is pressed to begin automatic concentration and elution of the water sample. Once the entire concentration and elution process is complete the display panel will read "Cycle Complete." The slide clamps on each bag are closed and the bags are removed and kept for analysis. The remainder of the set is discarded.

Currently, a system which simultaneously concentrates and recovers multiple types of microorganisms from large water volumes is not commercially available. A continuous flow centrifugation methodology which allows for the simultaneous concentration and processing of protozoa, bacteria, and viruses presented in large water volumes was developed according to the present invention.

Several stages of experimentation led to the development of the system. In order to test the method recovery efficiency, *Cryptosporidium* oocysts, *Bacillus anthracis* spores and MS2 bacteriophages were simultaneously spiked in 10-50 L tap and turbid surface water samples, resulting in mean recoveries of 40%, 35%, and 50% respectively.

The automated portable concentrator was challenged with small numbers of *Cryptosporidium* oocysts, *Bacillus anthracis* spores and MS2 bacteriophages simultaneously spiked in 10 L tap and turbid surface water samples, resulting in mean recoveries of 40%, 35%, and 50% respectively. The following is the summary of the results for 10 L of tap water.

TABLE 1

Recovery of *C. parvum* oocysts, MS2 bacteriophages and *B. anthracis* from 10 and 50 L tap water samples using a modified HS Core Bowl and a manually operated centrifuge.

| Vol. analyzed (L) (# replicates) | Spike dose oocysts (mean +/− SD) | Percent Recovery oocysts (mean +/− SD) | Spike dose pfu/mL (mean +/− SD) | Percent recovery pfu/mL (mean +/− SD) | Spike dose cfu (mean +/− SD) | Percent recovery cfu (mean +/− SD) |
|---|---|---|---|---|---|---|
| 10 (11) | 100 +/− 2.5 | 39.7 +/− 4.9 | $2.1 * 10^7$ +/− $8.3 * 10^6$ | 56.0 +/− 32.3 | 46.8 +/− 38.3 | 37.0 +/− 15.6 |
| 50 (3) | 100 +/− 2.5 | 31.3 +/− 9.0 | $1.0 * 10^7$ +/− $1.7 * 10^7$ | 71.1 +/− 50.0 | 12.7 +/− 15.9 | 59.6 +/− 4.3 |

TABLE 2

Recovery of *C. parvum* oocysts, MS2 bacteriophage and *B. anthracis* from 10 L tap water samples using a modified HS Core Bowl and an automated centrifuge.

| Vol. analyzed (L) (# replicates) | Spike dose oocysts (mean +/− SD) | Percent Recovery oocysts (mean +/− SD) | Spike dose pfu/m L (mean +/− SD) | Percent recovery pfu/m L (mean +/− SD) | Spike dose cfu (mean +/− SD) | Percent recovery cfu (mean +/− SD) |
|---|---|---|---|---|---|---|
| 10 (7) | 100 +/− 2.5 | 40.0 +/− 12.2 | $2.6 * 10^7$ +/− $1.3 * 10^7$ | 48.1 +/− 28.2 | 23.3 +/− 4.6 | 43.6 +/− 16.4 |

Tap water samples were obtained from the Division of Infectious Diseases, Cummings School of Vetinary Medicine. This tap water was supplied by the North Grafton Water Utility and is initially collected from a local ground water source. Turbidity of the sample was measured at 0.002 NTU by a DRT-15CE Tubidimeter, such as that manufactured by HF Scientific of Fort Meyers, Fla. Surface water samples were then collected from a near-by pond. The samples were autoclaved and the mean turbidity post sterilization was measured at 3 NTU.

Ten liters of each water matrix was transferred to sterile, disposable plastic cubitainers. The cubitainer was placed on a stir plate and stirred while being seeded with an aliquot of each representative organism and refilled with none liters of water once one liter of the original sample remained to be concentrated.

Prior to concentration the disposable harness is assembled in the machine according to the schematic layout of FIG. 10. Elution buffers are injected, for example, 5 ml of bacteria/protozoa and 20 ml of virus, into the designated bags using a Lauer lock syringe and the inlet tubing is placed into a 101 cubitainer containing the water sample. Referring to the flow chart of FIG. 11, the power source is turned on and the required protocol is selected. During concentration of the water sample, pathogens are retained inside the centrifuge bowl at 9000 RPM. The water sample is driven through the centrifuge bowl while it is spinning at 0.5 l/min by the peristaltic pump, which results in the retention of larger particles of protozoa and bacteria on the wall of the disposable centrifuge bowl. Small particles, such as virus, which escape the centrifugal forces are forced through the positively charged filter material in the out-flow chamber of the core and adsorbed to the material. After concentration of the water sample, the residual liquid in the bowl and the out-flow chamber of the core are subjected to an automated elution procedure that produces two separate volumes of bacteria/protozoa eluate, 300 ml, and virus eluate of 20 ml.

After concentration, the residual liquid is subject to a bacteria and protozoa elution cycle. 5 ml of elution buffer is delivered through the inlet port of the bowl from the designated PVC bag. The bacteria/protozoa elution buffer is a 5×PBS and 0.06% of a tween 80 solution is used as a detergent to dislodge bacteria and protozoa that have compacted to the walls of the bowl during the concentration process.

Once the elution buffer has been added, the centrifuge spins to a speed of 7000 rpm and then is immediately braked until it comes to a complete stop to dislodge the bacteria and protozoa. The cycle of spinning and braking is repeated ten times with a 10 second interval between each cycle. Upon completion of the final spin and brake cycle the 275 mL eluate is pumped from the inlet port of the bowl and returned to the PVC bag that originally contained the elution buffer. The centrifuge is then spun at 9000 rpm for 1 minute to extract any residual liquid from the out-flow chamber of the core, which is subsequently pumped from the inlet to the rest of the eluate. The entire volume, approximately 300 mL, is split into two separate volumes of 150 mL for analysis of bacteria and protozoa.

Following the bacteria and protozoa elution cycle, 10 mL of virus elution buffer is pumped into the out-flow chamber of the core through the outlet port of the bowl from the designated PVC bag. The virus elution buffer is a beef extract, glycine and Tween 80 protein solution (Scientific Methods, Granger, Ind.) used to neutralize the positive charge of the filter material inside of the core and dislodge the virus that were adhered during the concentration process.

After addition of the elution buffer, the filter material inside the core is saturated for 5 minutes at which point the centrifuge is spun for 1 minute at 9000 rpm to extract the liquid from the out-flow chamber of the core into the bowl. A second volume of 10 mL of virus buffer is pumped into to out-flow chamber and the process is repeated. The cycle ends by pumping the entire volume of virus eluate, approximately 20 mL, from the inlet port to the PVC bag that originally contained the virus elution buffer.

Certain microorganisms were used. *C. parvum* oocysts were chosen for use as representative protozoa. Water samples were spiked with one of two commercially available products. EasySeed, produced by Biotechnology Frontiers, LTD, NSW, Australia, consists of 1 00 flow-sorted; gamma irradiated *C. parvum* oocysts and *Giardia lamblia* cysts with a cell count standard deviation of less than 2.5 for each microorganism. Samples were spiked with EasySeed by decanting the contents of each vial as prescribed by the manufacturer. The second spiking suspension was produced by the Wisconsin State Laboratory of Hygiene, Madison, Wis., and consists of 100 *C. parvum* oocysts in 10 mL of reagent grade water and 0.01% Tween 20 with a cell count standard deviation of less than 2.5. The contents of one 10 mL tube was poured into the water sample and the tube was rinsed with 2 mL of 0.01% Tween 20 PBST followed by two 2 mL rinses of reagent grade water seeded the water samples. Each rinse was shaken vigorously for 30 seconds before being decanted into the water sample. Enumeration of the protozoa eluate from spiked water samples was performed as described by Method 1622 (USEPA, 2001). Dynabeads anti-*Cryptosporidium* Kit (Invitrogen Dynal AS, Oslo, Norway) was employed for selective separation of oocysts from water sample concentrates using immunomagnetic separation according to the manufacturers instructions. Crypt-A-Gb fluorescent monoclonal antibodies (Waterborne, Inc., New Orleans, La.) were used against *C. parvum* oocysts for detection and enumeration with a fluorescent microscope (Olympus Optical CO., Tokyo, Japan). The recovered numbers were multiplied by a factor of 2.

*B. anthracis* Sterne, a kanamycin resistant strain, was selected as representative bacteria. This strain of *B. anthracis* was constructed by the replacement of particular RNA coding sequences with an omega element, Q-kan, conferring kanamycin resistance. The stock suspension of *B. anthracis* was kept at −80° C. Each week during testing a spiking suspension was produced by diluting 100 μL of the stock suspension into 50 mL of maximum recovery diluent (Oxoid Ltd., Basingstoke, Hampshire, England) to an estimated concentration of 30 colony-forming units (cfu) per mL. Water samples were spiked by pipetting 1 mL of the spike suspension to the sample while stirring. The spike dose was quantitated by pipetting 1 mL of the spiking suspension to 50 mL of reagent grade water, vortexing and vacuum filtrating through a 0.45 μm, 47 mm membrane (Millipore, Billerica, Mass.). Post filtration, the membranes were placed on LB agar plates (Acros Organics, N.J.) containing kanamycin (Fisher Scientific, Fair Lawn, N.J.), inverted and incubated overnight at 37° C. After incubation, colony-forming units with the typical appearance of B. anthracis, opaque grey and white formations, were counted and recorded. To quantitate the recovery of B. anthracis from spiked water samples, the bacteria eluate was vacuum filtrated and incubated in the same manner. The recovered numbers were multiplied by a factor of 2.

Eschericlzia coli ATCC 15597: E. coli (American Type Culture Collection, Manassas, Va.) was used as host bacteria for MS2 bacteriophage. Freeze dried samples were purchased from ATCC, re-hydrated with 0.850 mL of LB broth (Acros Organics, NJ) and 150 mL of sterile glycerol, aliquoted to a volume of 50 μL and stored at −80° C. To propagate the bacteria one 50 μL aliquot was diluted in 10 mL of LB broth and incubated overnight at 37° C. and 200 RPM on a shaking incubator. After incubation 1.5 mL of sterile glycerol was added to the host bacteria broth, which was subsequently aliquoted to a volume of 200 μL and stored at −80° C. for no longer than one month. To quantitate the recovery of MS2 bacteriophage from spiked water samples and to enumerate the spike dose of phage LB agar plates were prepared with a field of actively growing E. coli to spot the phage on. Prior to preparation of the plates 800 μL of LB broth was added to one 200 μL aliquot of overnight grown E. coli and incubated for two hours at 37° C. After incubation, the host bacteria broth was spread evenly over an LB agar plate and the excess aspirated off. Serial dilutions of phage were than spotted onto the plate immediately after the E. coli had air-dried.

Results:

TABLE 3.1

Recovery of B. anthracis from 10 L tap water samples using a standard HS Core Bowl and a manually operated centrifuge.

| Vol. analyzed (L) (# replicates) | Spike dose cfu (mean +/− SD) | Percent Recovery cfu (mean +/− SD) |
|---|---|---|
| 10 (4) | 98.5 +/− 0.7 | 30.9 +/− 8.9 |
| 10 (10) | 58.4 +/− 9.6 | 30.9 +/− 10.8 |
| 10 (10) | 10.3 +/− 0.4 | 44.8 +/− 11.9 |

TABLE 3.2

Recovery of C. parvum oocysts and B. anthracis from 10 L tap water samples using a standard HS Core Bowl and an automated centrifuge.

| Vol. analyzed (L) (# replicates) | Spike dose oocysts (mean +/− SD) | Percent Recovery oocysts (mean +/− SD) | Spike dose cfu (mean +/− SD) | Percent recovery cfu (mean +/− SD) |
|---|---|---|---|---|
| 10 (5) | 100+/− 2.5 | 36.0+/− 15.2 | 14.8 +/− 3.8 | 90.2 +/− 9.0 |

TABLE 3.3

Recovery of C. parvum oocysts, MS2 bacteriophages and B. anthracis from 10 and 50 L tap water samples using a modified HS Core Bowl and a manually operated centrifuge.

| Vol. analyzed (L) (#replicates) | Spike dose oocysts (mean +/− SD) | Percent Recovery oocysts (mean +/− SD) | Spike dose pfu/mL (mean +/− SD) | Percent recovery pfu/mL (mean +/− SD) | Spike dose cfu (mean +/− SD) | Percent recovery cfu (mean +/− SD) |
|---|---|---|---|---|---|---|
| 10 (11) | 100 +/− 2.5 | 39.7 +/− 4.9 | $2.1 * 10^7$ +/− $8.3 * 10^6$ | 56.0 +/− 32.3 | 46.8 +/− 38.3 | 37.0 +/− 15.6 |
| 50 (3) | 100 +/− 2.5 | 31.3 +/− 9.0 | $1.0 * 10^7$ +/− $1.7 * 10^7$ | 71.1 +/− 50.0 | 12.7 +/− 15.9 | 59.6 +/− 4.3 |

TABLE 3.4

Recovery of C. parvum oocysts, MS2 bacteriophage and B. anthracis from 10 L tap water samples using a modified HS Core Bowl and an automated centrifuge.

| Vol. analyzed (L) (# replicates) | Spike dose oocysts (mean +/− SD) | Percent Recovery oocysts (mean +/− SD) | Spike dose pfu/mL (mean +/− SD) | Percent recovery pfu/mL (mean +/− SD) | Spike dose cfu (mean +/− SD) | Percent recovery cfu (mean +/− SD) |
|---|---|---|---|---|---|---|
| 10 (7) | 100 +/− 2.5 | 40.0 +/− 12.2 | $2.6 * 10^7$ +/− $1.3 * 10^7$ | 48.1 +/− 28.2 | 23.3 +/− 4.6 | 43.6 +/− 16.4 |

Although there have been major advancement in methodologies and equipment aimed at detecting waterborne pathogens, it is imperative that no matter how good the detection method is, an efficient sample concentration is required due to the small numbers of the target microorganisms. Moreover, most of the cutting edge detection technologies utilize portable detection equipment for field testing, but lack of an efficient portable sample concentrator restricts its use. Among the several approaches for an efficient sample concentration, continuous flow centrifugation appears to be very promising.

Although the present invention has been described in relation to particular embodiments thereof, many other variations and modifications and other uses will become apparent to those skilled in the art. It is preferred therefore, that the present invention be limited not by the specific disclosure herein, but only by the appended claims.

What is claimed is:

1. A device for concentrating multiple pathogens from large liquid samples comprising:
 a centrifuge bowl;
 a core located within the centrifuge bowl, the core comprising an outer core and an inner core, the outer core and the inner core comprising a core material having a plurality of holes in the core material;

a layer of positively charged filter material located between the outer core and the inner core;

an inner fluid passageway located within the core; and an inlet located at one end of the centrifuge bowl of receiving the liquid sample containing the pathogens and delivering the liquid sample to the core, and wherein the plurality of hole in the core material allows the liquid sample to flow through the core material to the positively charged material such the concentrated pathogens are attracted and adhere to the positively charge material.

2. The device of claim 1, further comprising a centrifuge, said centrifuge bowl being located within the centrifuge during concentration of the multiple pathogens.

3. The device of claim 1, wherein the multiple pathogens are from a group consisting of protozoa, bacteria, bacterial spores, and toxins.

4. The device of claim 1, wherein the inner core is spaced from and located within the outer core, wherein the positively charged material is located between the inner and outer cores.

5. An automated portable system for concentrating and eluting multiple pathogens from large liquid samples comprising:

a concentrator; and a sterile, disposable set including a high separation core centrifuge bowl, a plurality of collection bags, and tubing for connecting the collection bags to the core bowl and the liquid samples, wherein the core bowl includes a core located within the core bowl, the core comprising an inner core, an outer core and a layer of positively charged filter material located between the outer core and the inner core, the inner core and the outer core comprising a core material having a plurality of hole in the core material; and an inner fluid passageway located within the core; and an inlet located at on end of the bowl for receiving the liquid sample containing the pathogens and delivering the sample to the core, and wherein the plurality of holes in the material allows the liquid sample to flow through the core material and the positively charged material such that the concentrated pathogens are attracted and adhere to the positively charge material of the core.

6. The system of claim 5, wherein the concentrator includes a centrifuge and a pump, the core bowl being removably disposed in the centrifuge.

7. The device of claim 5, wherein the multiple pathogens are from a group consisting of protozoa, bacteria, bacterial spores, and toxins.

8. The device of claim 5, wherein the inner core is spaced from and located within the outer core, wherein the positively charged material is located between the inner and outer cores.

* * * * *